United States Patent [19]

Woltersdorf, Jr. et al.

[11] 4,003,927
[45] Jan. 18, 1977

[54] (1-OXO-7,8-DISUBSTITUTED-1,2,3,4-TETRAHYDRO-6-NAPHTHYLOXY)- AND (3,4-DISUBSTITUTED-5-OXO-6,7,8,9-TETRAHYDRO-5H-BENZOCYCLOHEPTENE-2-YLOXY) ACETIC ACIDS AND DERIVATIVES

[75] Inventors: Otto W. Woltersdorf, Jr., Chalfont; Edward J. Cragoe, Jr., Lansdale; Everett M. Schultz, Ambler; Gerald E. Stokker, Gwynedd Valley, all of Pa.

[73] Assignee: Merck & Co., Inc., Rahway, N.J.

[22] Filed: Oct. 12, 1973

[21] Appl. No.: 405,980

[52] U.S. Cl. .................... 260/520 D; 260/308 D; 260/475 SC; 260/473 F; 260/559 R; 424/269; 424/308; 424/317; 424/324
[51] Int. Cl.² ..................................... C07C 63/595
[58] Field of Search ............ 260/520, 473 F, 520 D

[56] References Cited

UNITED STATES PATENTS

| | | | |
|---|---|---|---|
| 3,369,025 | 2/1968 | Bolhofer | 260/520 |
| 3,668,241 | 6/1972 | Cragoe et al. | 260/520 |
| 3,704,314 | 11/1972 | Cragoe et al. | 260/520 |
| 3,776,944 | 12/1973 | Brown et al. | 260/520 |

OTHER PUBLICATIONS

Topless et al., J. Pharm. Sci. 57 (5) p. 737 (1968).
Burger, "Medicinal Chemistry" 3rd Ed. (1970) 64–72.

*Primary Examiner*—Norman Morganstern
*Attorney, Agent, or Firm*—Michael C. Sudol, Jr.; Edmunde Riedl; J. Jerome Behan

[57] ABSTRACT

(1-Oxo-7,8-disubstituted-1,2,3,4-tetrahydro-6-naphthyloxy)- and (3,4-disubstituted-5-oxo-6,7,8,9-tetrahydro-5H-benzocyclohepten-2-yloxy)acetic acids, their carboxylate salts, and the amide and 5-tetrazole derivatives thereof are active as diuretic and saluretic agents, which also have uricosuric activity.

1 Claim, No Drawings

(1-OXO-7,8-DISUBSTITUTED-1,2,3,4-TETRAHYDRO-6-NAPHTHYLOXY)- AND (3,4-DISUBSTITUTED-5-OXO-6,7,8,9-TETRAHYDRO-5H-BENZOCYCLOHEPTENE-2-YLOXY) ACETIC ACIDS AND DERIVATIVES

DISCLOSURE OF THE INVENTION

This invention relates to a new and useful class of compounds which are generally described as (1Oxo-7,8-disubstituted-1,2,3,4-tetrahydro-6-naphthyloxy)- and (3,4-disubstituted-5-oxo-6,7,8,9-tetrahydro-5H-benzocyclohepten-2-yloxy)acetic acids, their non-toxic carboxylate salts and the amide, N-loweralkylamide and N,N-diloweralkylamide and the derivatives where the carboxy group replaced by the 5-tetrazolyl radical. This invention also relates to novel methods for preparing these compounds.

The compounds of our invention are useful as diuretic and saluretic agents, and in addition, display uricosuric activity, which agents are valuable in the treatment of conditions associated with the retention of excess fluids and hypertension. When administered in therapeutic dosages, in conventional vehicles by a variety of routes, including oral and parenteral, these compounds of our invention are effective in reducing the sodium and chloride ion level in body fluids, and to lower dangerous levels of excess fluids to within more acceptable limits, and in general to alleviate those conditions usually associated with edema.

The compounds of our invention can be represented by the following formula:

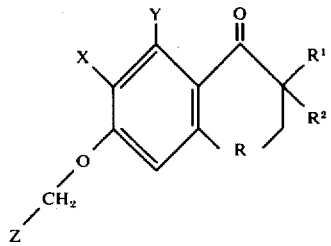

wherein R is methylene or ethylene; X is halogen, e.g., chloro and bromo or methyl; Y is a halogen or methyl; $R^1$ is loweralkyl, lowercycloalkyl, or hydrogen; $R^2$ is loweralkyl or hydrogen; and Z is carboxyl, carboxylate salts of physiologically acceptable non-toxic cations, carbamoyl, N-loweralkyl and N,N-diloweralkyl carbamoyl; and 5-tetrazolyl. When Z is hydrogen or cyano, the compounds represented constitute valuable intermediates for preparing the above diuretic and uricosuric compounds.

As used herein the term "loweralkyl" is intended to include $C_1$ to $C_4$ straight or branched chain alkyl groups such as methyl, ethyl, propyl, isopropyl, butyl, isobutyl, t-butyl and sec-butyl. The term "cycloloweralkyl" includes cyclopropyl, cyclobutyl, cyclopentyl, and cyclohexyl.

When R is methylene, Formula I represents the 1-oxo-7,8-disubstituted-1,2,3,4-tetrahydro-6-naphthyloxy compounds, and when R is ethylene, the 3,4-disubstituted-5-oxo-6,7,8,9-tetrahydro-5H-benzocyclohepten-2-yloxy compounds are shown.

Representative of the compounds included within Formula I are:
(1-oxo-7,8-dichloro-1,2,3,4-tetrahydro-6-naphthyloxy)-acetic acid;
(1-oxo-2-cyclopentyl-7,8-dichloro-1,2,3,4-tetrahydro-6-naphthyloxy) acetic acid;
(1-oxo-2-methyl-2-cyclopentyl-7,8-dichloro-1,2,3,6-tetrahydro-6-naphthyloxy) acetic acid;
(1-oxo-2-cyclopentyl-7,8-dimethyl-1,2,3,4-tetrahydro-6-napthyloxy) acetic acid;
(1-oxo-2-cyclopentyl-2,7,8-trimethyl-1,2,3,4-tetrahydro-6-naphthloxy) acetic acid;
)2-cyclopentyl-6-(5-tetrazolylmethoxy)-7,8-dichloro-1-tetralone;
N,N-diethyl-(1-oxo-2-cyclopentyl-7,8-dichloro-1,2,3,4-tetrahydro-6-naphthyloxy)acetamide;
3,4-dichloro-5-oxo-6,7,8,9-tetrahydro-5H-benzocyclohepten-2-yloxy)acetic acid;
3,4-dichloro-5-oxo-6-ethyl-6,7,8,9-tetrahydro-5H-benzocyclohepten-2-yloxy)acetic acid;
3,4-dichloro-5-oxo-6-cyclopentyl-6-methyl-6,7,8,9-tetrahydro-5H-benzocyclohepten-2-yloxy)acetic acid;
5-(3,4-dichloro-5-oxo-6-cyclopentyl-6,7,8,9-tetrahydro-5H-benzocyclohepten-2-yloxymethyl)tetrazole; and
3,4-dichloro-5-oxo-6-cyclopentyl-6-methyl-6,7,8,9-tetrahydro-5H-benzocyclohepten-2-yloxy)acetamide.

A preferred embodiment of this invention relates to the 1-oxo-7,8-dichloro-1,2,3,4-tetrahydro-6-naphthyloxy and 3,4-dichloro-5-oxo-6,7,8,9-tetrahydro-5H-benzocyclohepten-2-yloxy compounds of the structure

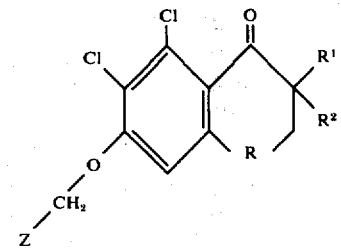

wherein R, $R^1$, $R^2$ and Z are as previously defined. These compounds of Formula II are particularly useful as diuretics and saluretics and represent a preferred class within the scope of this invention.

The intermediates for the compounds of Formula I are, in general, prepared by the cyclization of a compound having the structure.

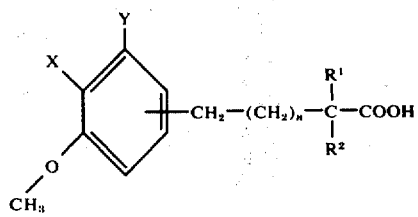

wherein X, Y, $R^1$, and $R^2$ have their previously defined meanings, and n is the integer 1, or 2.

In order to form the tetralone and benzosuberone cyclized intermediates from the acids of Formula III, a Fridel-Crafts catalyst such as stannic chloride, aluminum chloride, or polyphosphoric acid is employed. Preferably, the acids of Formula III are first converted to their acid chlorides by reaction with thionyl chloride or phosphorus pentachloride. This conversion to the acid chloride is conducted in a suitable solvent such as benzene at reflux until the reaction is complete, usually from 45 minutes to 2 hours. The solution comprising the acid chloride derivative of III is then cooled and a Friedel-Crafts catalyst added. This admixture is then heated to temperatures sufficient to achieve cyclization, usually 20°–25° C. being adequate, for a period of from 10 to 36 hours. The cyclized tetralone or benzosuberone intermediate is then isolated and purified.

In those instances where in Formula III, both X and Y are halogen, the ω-(3,4-dihalo-5-methoxyphenyl)-alkanoic acids can be employed giving the 7,8-dihalo-6-methoxy-2-R$^1$,R$^2$-1-tetralone and 2-methoxy-3,4-dihalo-6-R$^1$,R$^2$-6,7,8,9-tetrahydro-5H-benzocyclohepten-5-one.

These are converted to the 6-hydroxy and 2-hydroxy derivatives respectively by heating with pyridine hydrochloride at from 150°–190° C. for 1 to 2 hours, followed by collection and isolation of the products.

The 6-hydroxy and 2-hydroxy derivatives are then heated in a mixture of a suitable base such as potassium carbonate and an ester of acetic acid, e.g., loweralkyl haloacetate such as ethyl bromoacetate in a suitable solvent such as dimethylformamide at from 55°–60° C. for about 2 to 4 hours.

The aryloxyacetic acid ester thus formed is then hydrolyzed using an aqueous-methanol solution of an alkali hydroxide. Refluxing of the ester for about 1 to 2 hours is sufficient to effect the hydrolysis.

This gives the (1-oxo-2-R$^1$,R$^2$-7,8-dihalo-1,2,3,4-tetrahydro-6-naphthyloxy)acetic acids and the (3,4-dihalo-5-oxo-6-R$^1$,R$^2$-6,7,8,9-tetrahydro-5H-benzocyclohepten-2-yloxy)acetic acids. As shall be seen, these acetic acid derivatives can be further reacted to form amides, and substituted amides, as well as the other derivatives of this invention.

In those instances where in Formula III, X and Y are both halogen, it is suitable, although not preferable to employ the 2,3-disubstituted-4-methoxyphenylalkanoic acids as starting materials. However, when either X or Y is methyl, the availability of precursors requires that the 2,3-disubstituted-4-methoxyphenylalkanoic acids are employed. In this procedure the Friedel-Crafts cyclization is performed as previously described. The products resulting therefrom, however, have the oxo moiety misplaced for the purposes of this invention. That is, instead of 6-methoxy-7,8-X,Y-2-R$^1$,R$^2$-1-tetralone there is obtained 5-Y-6-X-7-methoxy-1-tetralone. This requires that intermediates cyclized from ω-(2-X,3-Y-5-methoxyphenyl)-alkanoic acids have the oxo moiety reduced by hydrogenation over a suitable hydrogenation catalyst, e.g., a noble metal. After reduction, the reduced product is oxidized by heating with chromium trioxide, and the resulting 6-methoxy-7-X,8-Y,1-tetralone and 2-methoxy-3-X,4-Y,6,7,8,9-tetrahydro-5H-benzocyclohepten-5-one intermediates can be alkylated or dialkylated to produce R$^1$ and R$^2$ substitutions in the compounds of Formula I where R$^1$ and R$^2$ are other than hydrogen. After alkylation, the compounds are further reacted as previously described.

A preferred technique for obtaining the acids of Formula III, especially when either R$^1$ or R$^2$ are other than hydrogen is to employ the reaction of an R$^1$ or R$^2$ substituted malonic ester, e.g. R$^1$, R$^2$ diethyl malonate, with a compound of Formula IV,

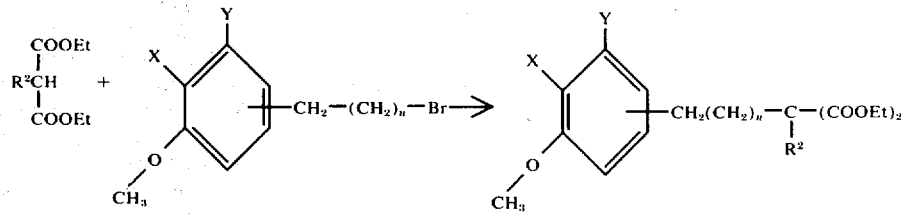

wherein X, Y and n are as defined, and Et is ethyl. Subsequent hydrolysis and decarboxylation through standard techniques of the malonic ester of a compound of Formula V produces the compounds of Formula III.

The 2-phenylethyl and 3-phenylpropyl halides represented by Formula IV, as well as the acids represented in Formula III are believed in themselves to be novel compounds and therefore their preparation is included below.

In general the compounds of Formulas III and IV are prepared from 2-X, 3-Y-anisoles, especially those derived from 2-ethyl-5-methoxy-6,7-dihalo-1-indanones.

First, the preparation of 2,3-dichloro-5-(2-bromoethyl)anisole from 2-ethyl-5-hydroxy-6,7-dichloro-1-indanone will be described.

EXAMPLE A 2,3-Dichloro-5-(2-bromoethyl)anisole

Step 1

2-Ethyl-5-methoxy-6,7-dichloro-1-indanone

A stirred mixture of 2-ethyl-5-hydroxy-6,7-dichloro-1-indanone (18.3 g., 0.075 mole), potassium carbonate (11.2 g., 0.08 mole) and methyl iodide (15 ml.) in dimethylformamide (DMF) (100 ml.) is warmed to 55° C. for two hours and poured into water (100 ml.). The 2-ethyl-5-methoxy-6,7-dichloro-1-indanone that separates melts at 146°–147° C. after crystallization from butyl chloride.

Step 2

3,4-Dichloro-5-methoxyphthalic acid

2-Ethyl-5-methoxy-6,7-dichloro-1-indanone (4 g.) is suspended in 200 ml. of water containing 1 ml. of 20% sodium hydroxide. The mixture is heated to boiling and potassium permanganate (18 g.) is added portion-wise over a four-hour period in such a manner that each time the purple color disappears an additional portion is added. A few drops of methanol are added to destroy the excess permanganate and the manganese oxide is removed by filtration. The colorless filtrate is acidified with 6 N HCl and evaporated to dryness under reduced pressure. The solid residue is extracted with boiling acetone and the extract is evaporated to dryness. The residue (2.57 g.) is suspended in 6 N HCl (125 ml.) and the mixture is boiled for 10 minutes, cooled and the 3,4-dichloro-5-methoxyphthalic acid is collected. On heating the product in a capillary melting point tube, it evolves a gas at 210° C. (formation of the anhdride), resolidifies and melts at 218°–220° C.

Step 3

3,4-Dichloro-5-hydroxybenzoic acid 3,4-Dichloro-5-methoxyphthalic acid (17.5 g., 0.066 mole) is mixed with pyridine hydrochloride (120 g.). The mixture is heated at 180° C. for one hour and then poured into water (1 l.). The solid that separates melts at 211°–212..5° C. and is used without purification in the next step.

Step 4

3,4-Dichloro-5-methoxybenzoic acid

A stirred mixture of the product of step 3 (10.9 g., 0.0623 mole), potassium carbonate (20.7 g., 0.150 mole and methyl iodide (42.6 g., 0.3 mole) in dimethylformamide, (DMF) (100 ml.) is heated at 60° C. for three hours. A solution is prepared by dissolving potassium hydroxide (8.4 g., 0.150 mole) in a minimum of water, then methanol (300 ml.) is added. The mixture is refluxed for one-half hour and poured into water (2 l.). The mixture is heated to 80° C., filtered and acidified with 12 N HCl. There is obtained 11.0 g. of 3,4-dichloro-5-methoxybenzoic acid, melting point 218°–219° C.

Step 5

3,4-Dichloro-5-methoxybenzoyl chloride 3,4-Dichloro-5-methoxybenzoic acid (22.1 g., 0.1 mole) is heated with thionyl chloride (15 g., 0.125 mole) in benzene (100 ml.) until evolution of sulfur dioxide and hydrogen chloride ceases. The benzene and excess thionyl chloride are evaporated and the solid residue is used in the next step.

Step 6

Ethyl 3,4-dichloro-5-methoxyphenylacetate

A solution of 3,4-dichloro-5-methoxybenzoyl chloride (22.7 g., 0.1 mole) in absolute ether (100 ml.) is added at 5°–10° C. to a solution of diazomethane from 35 g. of nitroso-methylurea in 500 ml. of absolute ether. The mixture is kept for 24 hours and the ether is removed under reduced pressure. A yellow solid, a diazoketone, remains.

The diazoketone (12.2 g., 0.05 mole) is dissolved in absolute ethanol (50 ml.). To this solution is added a small portion of a slurry of silver oxide (5.5 g.) in ethanol (30 ml.) When the evolution of nitrogen slackens, an additional portion of silver oxide is added and so on until all of the slurry has been added. The mixture then is heated to reflux for a few minutes and then is treated with charcoal, filtered and evaporated. The crude ethyl 3,4-dichloro-5-methoxyphenylacetate that remains is purified by distillation.

Step 7

2-(3,4-Dichloro-5-methoxyphenyl)ethanol

Lithium aluminum hydride (1.2 g., 0.032 moles) is suspended in dry ether (100 ml.) in a flask equipped with a stirrer, dropping funnel and protected from moisture. To this is added dropwise with stirring a solution of ethyl 3,4-dichloro-5-methoxyphenylacetate (4.1 g., 0.0156 mole) in dry ether (150 ml.) over a 20-minute period. The mixture is stirred for an additional 30 minutes. Then, with vigorous stirring 1.2 g. of water is added carefully followed by 15% sodium hydroxide (1.5 ml.) and an additional 4.5 ml. of water. The ether solution is filtered from the granular inorganic salts which then are washed with additional ether. The combined ether solutions are washed with water and dried (Na$_2$SO$_4$). Upon evaporation of the ether, 2-(3,4-dichoro-5-methoxyphenyl)ethanol remains.

Step 8

2,3-Dichloro-5-(2-bromoethyl)anisole

In a four-necked flask fitted with a stirrer, internal thermometer, dropping funnel and calcium chloride tube is placed freshly distilled phosphorous tribromide (9.6 g., 0.036 mole) and dry toluene (50 ml.). To this is added dry pyridine (1.5 g.). The mixture is stirred for 15 minutes and then cooled to −5° C. A mixture of 2-(3,4-dichloro-5-methoxyphenyl)ethanol (22.1 g., 0.1 mole) and dry pyridine (0.5 g.) in toluene (50 ml.) is added dropwise with stirring at −5° to −3° C. over a one hour period. The reaction mixture is stirred at −5° to −3° C. for an additional hour and then allowed to warm up to 20°–25° C. The mixture is kept for 48 hours and then added to ice water (ca. 500 ml.). The toluene layer is separated and washed with water, dilute hydrochloric acid, sodium bicarbonate solution and again with water. After drying over Na$_2$SO$_4$ and evaporation of the toluene under reduced pressure there is obtained 2,3-dichloro-5-(2-bromoethyl)anisole.

EXAMPLE B 5-(3,4-Dichloro-5-methoxyphenyl)valeric acid

Step 1

3,4-Dichloro-5-methoxybenzaldehyde 3,4-Dichloro-5-methoxybenzoic acid (1.7 g., 0.0077 mole) as obtained in Example A, Step 4, in thionyl chloride (20 ml.) is heated at reflux for 45 minutes. The solution is then evaporated to dryness under reduced pressure, benzene (25 ml.) is added and likewise evaporated. The residue is dissolved in xylene (20 ml.) and 5% PdCl$_2$ on BaSO$_4$ (0.2 g.) and Rosenmund poison (Organic Reactions Vol. 4, p. 367) (1 drop from a solution of 1 drop of standard solution diluted with 500 ml. of xylene) is added. The mixture is heated to reflux and hydrogen is bubbled through the mixture until hydrogen chloride is no longer evolved (ca. three hours).

The catalyst is removed by filtration and washed in the filter with benzene. The filtrate and washings are washed with water and saturated brine, dried over Na$_2$SO$_4$ and evaporated. The residue is crystallized from hexane to obtain 3,4-dichloro-5-methoxybenzaldehyde (0.6 g.), melting point 97°–98.5° C.

Step 2

5-(3,4-Dichloro-5-methoxyphenyl)penta-2,4-dienoic acid 3,4-Dichloro-5-methoxybenzaldehyde (29 g., 0.14 mole) and methyl crotonate (21.5 g., 0.21 mole) in t-butyl alcohol (50 ml.) are added dropwise to a stirred solution of potassium (11.5 g., 0.38 mole) in t-butyl alcohol (200 ml.) and stirring is continued for 4 hours after the addition. Most of the t-butyl alcohol then is evaporated, the residue is added to ice water (ca. 500 ml.) and the mixture is acidified with 12 N HCl. The product, which consists of a mixture of the title acid and its methyl ester, is extracted with chloroform. The extract is dried (Na$_2$SO$_4$) and evaporated.

The residue is refluxed for 15 hours in a mixture of potassium hydroxide (8 g.), water (300 ml.) and methanol (100 ml.). The methanol is evaporated and the aqueous solution is filtered and acidified with 12 N HCl to obtain 5-(3,4-dichloro-5-methoxyphenyl)penta-2,4-dienoic acid.

Step 3

5-(3,4-Dichloro-5-methoxyphenyl)valeric acid 5-(3,4-Dichloro-5-methoxyphenyl)penta-2,4-dienoic acid (27.3 g., 0.1 mole) in ethanol (300 ml.) containing 96% sulfuric acid (30 ml.) is hydrogenated over rhodium on carbon (5%) (2 g.) at an initial pressure of 45 psi. After removal of the catalyst, the ethanolic solution is added to ice water (ca. 500 ml.) and the sulfuric acid is neutralized with 40% sodium hydroxide. The alcohol is removed by distillation at reduced pressure. The aqueous remainder is made acid with 6 N HCl and extracted with ether. The ether extract is washed with water and saturated brine and dried over $Na_2SO_4$. On evaporation of the ether 5-(3,4-dichloro-5-methoxyphenyl)valeric acid is obtained.

Alternatively, the 3,4-dichloro-5-methoxybenzaldehyde of Example B, Step 1, can be reacted as follows in Example C.

EXAMPLE C 2,3-Dichloro-5-(3-bromopropyl)anisole

Step 1

Ethyl 3,4-dichloro-5-methoxycinnamate

In a 300 ml. three-necked flask equipped with a reflux condenser, dropping funnel and mechanical stirrer is placed 40 ml. of dry xylene and 2.9 g. (0.126 g. atom) of clean sodium. The flask is heated in an oil bath until the sodium is melted. The stirrer is then started and the sodium is whipped into very small globules. The oil bath is removed and stirring is continued until the sodium solidifies in a powdered form. The xylene is decanted and ethyl acetate (46 ml., 0.47 mole) containing absolute ethanol (ca. 0.4 ml.) is added to the sodium. The flask is cooled quickly to 0° C. and 3,4-dichloro-5-methoxybenzaldehyde (20.5 g., 0.1 mole as obtained in Example C, Step 1, in 40 ml. of ethyl acetate is added slowly while the mixture is stirred and kept at 0°-5° C. Stirring then is continued until all but a trace of sodium has reacted.

Any excess sodium is destroyed by the careful addition of acetic acid (9–10 ml.) and the mixture is diluted with water. The ester layer is separated and the water layer is extracted with ethyl acetate. The combined ester extracts are washed with 6 N HCl and dried over sodium sulfate. The ethyl acetate then is evaporated to obtain ethyl 3,4-dichloro-5-methoxycinnamate.

Step 2

3-(3,4-Dichloro-5-methoxyphenyl)propanol

Lithium aluminum hydride (1.2 g., 0.032 mole) is suspended in dry ether (100 ml.) in a flask equipped with a stirrer, upright condenser and dropping funnel and protected from moisture. To this is added dropwise with stirring a solution of ethyl 3,4-dichloro-5-methoxycinnamate (4.3 g., 0.0156 mole) in dry ether (150 ml.) over a twenty minute period. The mixture is stirred for an additional 30 minutes. Then with vigorous stirring, 1.2 g. of water is added carefully followed by 15% sodium hydroxide (1.5 ml.) and an additional 4.5 ml. of water. The ether solution is filtered from the granular inorganic salts which then are washed with additional ether. The combined ether solutions are washed with water and dried ($Na_2SO_4$). Upon evaporation of the ether 3-(3,4-dichloro-5-methoxyphenyl)propanol remains.

Step 3

2,3-Dichloro-5-(3-bromopropyl)anisole

In a four-necked flask fitted with a stirrer, internal thermometer, dropping funnel and calcium chloride tube is placed freshly distilled phosphorus tribromide (9.6 g., 0.036 mole) and dry toluene (50 ml.). To this is added dry pyridine (1.5 g.). The mixture is stirred for 15 minutes and then cooled to −5° C. A mixture of the product of Step 2 (23.5 g., 0.1 mole) and pyridine (0.5 g.) in toluene (50 ml.) is added dropwise with stirring at −5° C. to −3° C. over a one hour period. The reaction mixture is stirred at −5° C. to −3° C. for an additional hour and then allowed to warm up to 20°–25° C. The mixture is kept for 48 hours and then added to ice water (ca. 500 ml.). The toluene layer is separated and washed with water, dilute hydrochloric acid, sodium bicarbonate solution and again with water. After drying over $Na_2SO_4$ and evaporation of the toluene under reduced pressure there is obtained 2,3-dichloro-5-(3-bromopropyl)anisole.

The following example further illustrates the preparation of starting material from 2-X,3-Y-anisoles.

EXAMPLE D 4-(2,3-Dichloro-4-methoxyphenyl)butyric acid

Step 1

3-(2,3-Dihcloro-4-methoxybenzoyl)propionic acid

Powdered aluminum chloride (270 g., 2 moles) is added slowly at 0° C. to a stirred mixture of 2,3-dichloroanisole (177 g., 1.0 mole) and succinic anhydride (100 g., 1.0 mole) in methylene chloride (800 ml.). The mixture then is stirred at 0° C. for two hours, then at 20°–25° C. for 16 hours and then refluxed for one hour and poured into ice cold 1 N HCl (2.4 l.). The aqueous mixture is heated to 65° C. and allowed to cool to 20° C. The sticky solid that separates is triturated with warm butyl chloride to obtain 136 g. product, melting point 140°–145° C. After crystallization from ethanol-water (5:7) there is obtained 3-(2,3-dichloro-4-methoxybenzoyl)propionic acid (125 g.), melting point 142°–144° C..

Step 2

4-(2,3-Dichloro-4-methoxyphenyl)butyric acid

A mixture of 3-(2,3-dichloro-4-methoxybenzoyl)propionic acid (125 g.), 0.45 mole), amalgamated zinc (500 g.) and 12 N HCl (600 ml.) is stirred at 20°–25° C. for two hours and then refluxed for 16 hours. An additional 100 ml. of 12 N HCl is added and refluxing is continued for five hours. The mixture then is cooled and diluted with water (2 l.). The product is extracted with chloroform. The extract is washed with water and dried over sodium sulfate and evaporated. The residue is crystallized from ethanol-water (1:1) to obtain 4-(2,3-dichloro-4-methoxyphenyl)butyric acid (103.7 g.), melting point 120°–123° C.

It is equally suitable to employ an equimolar amount of 2,3-dimethylanisole, or 2-halo-3-methylanisoles such as 2-chloro-3-methylanisole; and 2-methyl-3-haloanisoles such as 2-methyl-3-chloroanisole in Step 1 in place of the 2,3-dichloroanisole used therein to obtain the corresponding 3-(2,3-dimethyl-4-methoxybenzoyl)propionic acid, 3-(2-chloro-3-methyl-4-methoxybenzoyl)propionic acid and 3-(2-methyl-3-chloro-4-methoxybenzoyl)propionic acid, which, in turn, are used in equimolar amount to substitute for the 3-(2,3-dichloro-4-methoxybenzoyl)propionic acid used in Step 2 to obtain the corresponding 4-(2,3-dimethyl-4-methoxyphenyl)butyric acid, 4-(2-chloro-3-methyl-4-methoxyphenyl)butyric acid; and 4-(2-methyl-3-chloro-4-methoxyphenyl)butyric acid.

In the same manner there can be obtained the corresponding valeric acids by substituting for the succinic anhydride an equimolar amount of glutaric anhydride.

Now having described the preparation of starting materials, the following examples will serve to further illustrate the compounds of our invention.

EXAMPLE I (1-Oxo-2-cyclopentyl-7,8-dichloro-1,2,3,4-tetrahydro-6-naphthyloxy)acetic acid Step 1

Diethyl [2-(3,4-dichloro-5-methoxyphenyl)ethyl]cyclopentylmalonate 2,3-Dichloro-5-(2-bromoethyl)anisole (28.4 g., 0.088 mole) as obtained in Intermediate Example A, Step 8, and diethyl cyclopentyl malonate (24 g., 0.106 mole) in dry ethanol are added dropwise to a boiling solution of dry ethanol containing dissolved sodium (2.024 g., 0.088 g. atom). The mixture is refluxed until it is no longer basic. The alcohol then is removed by distillation, the precipitated sodium bromide is dissolved by the addition of water and the mixture is extracted with a suitable solvent such as ether or benzene. The extracts are combined, washed with water and dried over $Na_2SO_4$. Evaporation of the solvent provides diethyl [2-(3,4-dichloro-5-methoxyphenyl)ethyl]cyclopentylmalonate.

Step 2

2-Cyclopentyl-4-(3,4-dichloro-5-methoxyphenyl)-butanoic acid

Diethyl [2-(3,4-dichloro-5-methoxyphenyl)ethyl]-cyclopentylmalonate (28 g., 0.065 mole) is refluxed in an aqueous methanolic solution of potassium hydroxide (5.6 g., 0.1 mole) for five hours. The methanol then is distilled and the residue is diluted with water, filtered and acidified. The mixture is extracted with a suitable solvent such as ether, benzene or chloroform. The extracts are washed with water and dried over sodium sulfate. The solvent is evaporated and the substituted malonic acid so obtained is heated to a point where carbon dioxide is evolved and kept at this temperature, until evolution of carbon dioxide ceases, to obtain 2-cyclopentyl-4-(3,4-dichloro-5-methoxyphenyl)-butanoic acid.

Step 3

2-Cyclopentyl-6-methoxy-7,8-dichloro-1-tetralone

2-Cyclopentyl-4-(3,4-dichloro-5-methoxyphenyl)-butanoic acid (13.1 g., 0.04 mole), dry benzene (100 ml.) and phosphorous pentachloride (7.5 g., 0.034 mole) are refluxed for one hour with stirring. The mixture is cooled to 5° C. and anhydrous stannic chloride (5 ml.) in dry benzene (25 ml.) is added portionwise. The mixture is allowed to warm to 20°–25° C. and kept for 24 hours after which it is poured into ice water. The organic material is extracted with a suitable solvent. The extract is washed, dried and evaporated to obtain 2-cyclopentyl-6-methoxy-7,8-dichloro-1-tetralone.

Step 4

2-Cyclopentyl-6-7,8-dichloro-1-tetralone

2-Cyclopentyl-6-methoxy-7,8-dichloro-1-tetralone (6.58 g., 0.02 mole) is mixed with pyridine hydrochloride (60 g.) and the mixture is heated at 180° C. for one hour. The mixture is poured into water (ca. 400 ml.). The solid that separates is collected, washed with water and air dried to obtain 2-cyclopentyl-6-hydroxy-7,8-dichloro-1-tetralone.

Step 5

(1-Oxo-2-cyclopentyl-7,8-dichloro-1,2,3,4-tetrahydro-6-naphthyloxy)acetic acid

2-Cyclopentyl-6-hydroxy-7,8-dichloro-1-tetralone (9.45 g., 0.03 mole) is heated in a mixture of potassium carbonate (5.52 g.) and ethyl bromoacetate (6.68 g., 0.04 mole) in DMF 70 ml.) at 55°–60° C. for three hours. Potassium hydroxide (2.24 g., 0.04 mole) is added. This solution is added to the reaction mixture and the whole is refluxed for 1 hour. Most of the methanol is evaporated and the residue is added to water (ca. 200 ml.). The solid that separates upon acidification is collected, washed with water and crystallized from ethanol to obtain (1-oxo-2-cyclopentyl-7,8-dichloro-1,2,3,4-tetrahydro-6-naphthyloxy)acetic acid.

EXAMPLE II (1-Oxo-7,8-dichloro-1,2,3,4-tetrahydro-6-naphthyloxy)-acetic acid

Step 1

5,6-Dichloro-7-methoxy-1-tetralone 4-(2,3-Dichloro-4-methoxyphenyl)butyric acid (103.7 g., 0.394 mole) as obtained in Intermediate Example D, Step 2, in thionyl chloride (250 ml.) is refluxed for 45 minutes. The excess thionyl chloride is evaporated under reduced pressure and the residual acid chloride is dissolved in methylene chloride (1 l.). The solution is cooled to 5° C. and aluminum chloride (53.4 g., 0.4 mole) is added gradually with stirring. The mixture then is stirred at 20°–25° C. for 20 hours, heated to reflux, cooled and poured into a mixture of ice water (4 l.). and 12 N HCl (400 ml.). The organic layer is separated and washed with water, 5% sodium hydroxide, saturated brine and dried over $MgSO_4$. Upon evaporation of the solvent a pale yellow solid is obtained. On crystallization from ethanol water (5:1) there is obtained 5,6-dichloro-7-methoxy-1-tetralone (77.7 g.), melting point 150°–151° C.

Step 2

5,6-Dichloro-7-methoxytetralin 5,6-Dichloro-7-methoxy-1-tetralone (20 g., 0.08 mole) dissolved in acetic acid (300 ml.) is hydrogenated over 5% palladium on carbon (12 g.). The catalyst is removed and washed well with acetic acid. The combined acetic acid fractions are evaporated to dryness and the residue is crystallized from hexane to obtain 5,6-dichloro-7-methoxytetralin (17 g.), melting point 67°–68.5° C.

Step 3

6-Methoxy-7,8-dichloro-1-tetralone

Chromium trioxide (28 g., 0.028 mole) in 83% acetic acid (12 ml.) is added slowly at 0° C. to a stirred solution of 5,6-dichloro-7-methoxytetralin (4 g., 0.073 mole) in a mixture of acetic acid (90 ml.) and propionic acid (20 ml.). The resulting dark mixture then is kept for 20 hours at 20°–25° C. The resulting dark green solution is poured into a mixture of water (900 ml.) and 96% $H_2SO_4$ (10 ml.). The mixture is heated to 70° C., cooled to 0° C. and the precipitate is collected, washed with water, and dried. The dried product is sublimed twice at 100° C. at ca. 0.5 mm. and then crystallized from methanol to obtain 6-methoxy-7,8-dichloro-1-tetralone (1 g.), melting point 132°–132.5° C. The identity of the product is established by proton magnetic resonance (pmr).

Step 4

6-Hydroxy-7,8-dichloro-1-tetralone

A mixture of 6-methoxy-7,8-dichloro-1-tetralone (2.45 g.) and pyridine hydrochloride (25 g.) is heated at 180°–190° C. for two hours and then poured into water (500 ml.). The product is collected, washed with water, dried and crystallized from ethanol-water (3:2) to obtain 6-hydroxy-7,8-dichloro-1-tetralone (1 g.), melting point 243.5°–245.5° C.

Step 5

(1-Oxo-7,8-dichloro-1,2,3,4-tetrahydro-6-naphthyloxy)-acetic acid

A stirred mixture of 6-hydroxy-7,8-dichloro-1-tetralone (1 g., 0.0044 mole), potassium carbonate (10.69 g., 0.005 mole) and ethyl bromoacetate (0.84 g., 0.005 mole) in DMF (20 ml.) is heated at 60° C. for 1½ hours. A solution of potassium hydroxide (0.45 g., 0.008 mole) in methanol (40 ml.) is added, the mixture is refluxed for one-half hour and then poured into water (ca. 500 ml.). Upon acidification a white powder separates. It is collected, washed with water, dried and crystallized from ethanol to obtain (1-oxo-7,8-dichloro-1,2,3,4-tetrahydro-6-naphthyloxy)-acetic acid (1.1 g.), melting point 250°–252° C.

| Anal. | C | H |
|---|---|---|
| Calc'd. | 49.58 | 3.49 |
| Found | 49.73 | 3.63 |

In an analogous manner, but employing
4-(2,3-dimethyl-4-methoxyphenyl)butyric acid;
4-(2-chloro-3-methyl-4-methoxyphenyl)butyric acid;
4-(2-methyl-3-chloro-4-methoxyphenyl)butyric acid;
there are obtained respectively:
(1-Oxo-7,8-dimethyl-1,2,3,4-tetrahydro-6-naphthyloxy)-acetic acid;
(1-Oxo-7-chloro-8-methyl-1,2,3,4-tetrahydro-6-naphthyloxy)-acetic acid;
(1-Oxo-7-methyl-8-chloro-1,2,3,4-tetrahydro-6-naphthyloxy)-acetic acid.

EXAMPLE III (1-Oxo-2-methyl-2-cyclopentyl-7,8-dichloro-1,2,3,4-tetrahydro-6-naphthyloxy)acetic acid Step 1

2-Cyclopentyl-2-methyl-6-methoxy-7,8-dichloro-1-tetralone

2-Cyclopentyl-6-methoxy-7,8-dichloro-1-tetralone (14.4 g., 0.046 mole) as obtained in Example I, Step 3 is dissolved in t-butyl alcohol (250 ml.). A stream of nitrogen is lead through the flask and the mixture is heated to reflux. Then a solution of potassium t-butoxide (7.5 g., 0.067 mole) dissolved in t-butyl alcohol (175 ml.) is added rapidly. The dark solution is refluxed for 1 hour, then cooled to 20° C. and methyl iodide (14.2 g., 0.01 mole) is added. The mixture is refluxed for 10 minutes. Potassium bromide precipitates and the mixture becomes lighter in color. The mixture is cooled, water (25 ml.) is added and the mixture is evaporated to dryness. The crude product is collected, washed with water and air dried to obtain 2-cyclopentyl-2-methyl-6-methoxy-7,8-dichloro-1-tetralone.

Step 2

2-Cyclopentyl-2-methyl-6-hydroxy-7,8-dichloro-1-tetralone

By the process of Example I, Step 4, but substituting for the 2-cyclopentyl-6-methoxy-7,8-dichloro-1-tetralone there used, an equivalent amount of 2-cyclopentyl-2-methyl-6-methoxy-7,8-dichloro-1-tetralone, there is obtained 2-cyclopentyl-2-6-hydroxy-7,8-dichloro-1-tetralone.

Step 3

(1-Oxo-2-methyl-12-cyclopentyl-7,8-dichloro-1,2,3,4-tetrahydro-6-naphthyloxy)acetic acid By the process of Example I, Step 5, but substituting for the 2-cyclopentyl-6-hydroxy-7,8-dichloro-1-tetralone there used an equivalent amount of 2-cyclopentyl-2-methyl-6-hydroxy-7,8-dichloro-1-tetralone there is obtained (1-oxo-2-methyl-2-cyclopentyl-7,8-dichloro-1,2,3,4-tetrahydro-6-naphthyloxy)acetic acid.

EXAMPLE IV

2-Cyclopentyl-6-(5-tetrazolylmethoxy)-7,8-dichloro-1-tetralone

Step 1

2-Cyclopentyl-6-cyanomethoxy-7,8-dichloro-1-tetralone

A stirred mixture of 2-cyclopentyl-6-hydroxy-7,8-dichloro-1-tetralone (2.9 g., 0.1 mole), potassium carbonate (15.2 g., 0.11 mole) and chloroacetonitrile (7.5 g., 0.10 mole) in DMF (100 ml.) is heated at 55°–60° C. for two hours and poured into water. The 2-cyclopentyl-6-cyanomethoxy-7,8-dichloro-1-tetralone that separates is collected and dried.

Step 2

2-Cyclopentyl-6-(5-tetrazolylmethoxy)-7,8-dichloro-1-tetralone

To 2-cyclopentyl-6-cyanomethoxy-7,8-dichloro-1-tetralone (5.6 g., 0.0165 mole) in DMF (25 ml.) is added sodium azide (12.6 g., 0.0194 mole) and ammonium chloride (1.05 g., 0.0194 mole). The mixture is heated at 85°–90° C. for one hour, cooled and poured into ice water. The mixture is acidified with 6 N HCl. The dark gummy solid that forms is triturated with butyl chloride to obtain a solid, which is crystallized from a mixture of butyl chloride and methanol to obtain 2-cyclopentyl-6-(5-tetrazolylmethoxy)-7,8-dichloro-1-tetralone.

EXAMPLE V (1-Oxo-2-cyclopentyl-7,8-dimethyl-1,2,3,4-tetrahydro-6-naphthyloxy) acetic acid Step 1

5,6-Dimethyl-7-methoxy-1-tetralone

By the procedure of Example II, Step 1, but substituting for the 4-(2,3-dichloro-4-methoxyphenyl)- butyric acid, there used, an equivalent amount of 4-(2,3-dimethyl-4-methoxyphenyl)butyric acid, there is obtained 5,6-dimethyl-7-methoxy-1-tetralone.

Step 2

1,2-Dimethyl-3-methoxytetralin

By the process of Example II, Step 2, but substituting for the 5,6-dichloro-7-methoxy-1-tetralone used therein an equivalent amount 5,6-dimethyl-7-methoxy-1- tetralone, then 1,2-dimethyl-3-methoxytetralin is obtained.

Step 3

6-Methoxy-7,8-dimethyl-1-tetralone

By the process of Example II, Step 3, but substituting for the 5,6-dichloro-7-methoxytetralin used therein an equivalent amount of 1,2-dimethyl-3-methoxytetralin, then 6-methoxy-7,8-dimethyl-1-tetralone is obtained.

Step 4

2-Cyclopentyl-6-methoxy-7,8-dimethyl-1-tetralone

By the procedure of Example III, Step 1, but substituting for the 2-cyclopentyl-6-methoxy-7,8-dichloro-1-tetralone used therein an euivalent amount of 6-methoxy- 7,8-dimethyl-1-tetralone, and for the methyl iodide there used an equivalent amount of cyclopentyl bromide, then 2-cyclopentyl-6-methoxy-7,8-dimethyl-1-tetralone is obtained.

Step 5

2-Cyclopentyl-6-hydroxy-7,8-dimethyl-1-tetralone

By the process of Example II, Step 4, but substituting for the 6-methoxy-7,8-dichloro-1-tetralone used therein an equivalent amount of 2-cyclopentyl-6-methoxy- 7,8-dimethyl-1-tetralone, then 2-cyclopentyl-6-hydroxy-7,8- dimethyl-1-tetralone is obtained.

Step 6

(1-Oxo-2-cyclopentyl-7,8-dimethyl-1,2,3,4-tetrahydro-6- naphthyloxy) acetic acid By the process of Example II, Step 5, but substituting for the 6-hydroxy-7,8-dichloro-1-tetralone used therein an equivalent amount of 2-cyclopentyl-6-hydroxy-7,8-dimethyl-1-tetralone, then (1-oxo-2-cyclopentyl-7,8-dimethyl- 1,2,3,4-tetrahydro-6-naphthyloxy) acetic acid is obtained.

EXAMPLE VI (3,4-Dichloro-5-oxo-6,7,8,9-tetrahydro-5H-benzocyclohepten- 2-yloxy acetic acid Step 1

2-Methoxy-3,4-dichloro-6,7,8,9-tetrahydro-5H-benzocyclohepten- 5-one 5-(3,4-dichloro-5-methoxyphenyl) valeric acid (11 g. 0.04 mole) as obtained in Intermediate Example B, Step 3, dry benzene (100 ml.) and phosphorous pentachloride (7.5 g., 0.034 mole) are refluxed for one hour with stirring. The mixture is cooled to 5° C. and anhydrous stannic chloride (5 ml.) in dry benzene (25 ml.) is added portionwise. The mixture is allowed to warm to 20°–25° C. and kept for 24 hours after which it is poured into ice water. The organic material is extracted with a suitable solvent. The extract is washed, dried and evaporated to obtain 2-methoxy-3,4-dichloro-6,7,8,9-tetrahydro-5H-benzocyclohepten-5-one.

Step 2

2-Hydroxy-3,4-dichloro-6,7,8,9-tetrahydro-5H-benzocyclohepten- 5-one

2-Methoxy-3,4-dichloro-6,7,8,9-tetrahydro-5H- benzocyclohepten-5-one (25.9 g., 0.1 mole) intimately mixed with pyridine hydrochloride (250 g.) is heated at 180° C. for 1 hour. The hot mixture is poured into water whereupon 2-hydroxy-3,4-dichloro-,6,7,8,9-tetrahydro-5H-benzocyclohepten- 5-one separates and is isolated in the usual way.

Step 3

(3,4-Dichloro-5-oxo-6,7,8,9-tetrahydro-5H-benzocyclohepten- 2-yloxy)acetic acid

2-Hydroxy-3,4-dichloro-6,7,8,9-tetrahydro-5H- benzocyclohepten-5-one (10 g., 0.04 mole), anhydrous potassium carbonate (7 g., 0.05 mole) and ethyl bromoacetate (8.35 g., 0.05 mole) in DMF (75 ml.) are stirred at 60° C. for 1 hour. Then potassium hydroxide (5 g.) dissolved in water (5 ml.) and methanol (100 ml.) is added. The mixture is refluxed for one hour. The methanol is distilled, the residue is poured into water, and the solution is filtered. Upon acidification with 12 N HCl, (3,4-dichloro-5-oxo-6,7,8,9-tetrahydro-5H-benzocyclohepten- 2-yloxy)acetic acid separates and is collected by filtration.

EXAMPLE VII (3,4-Dichloro-5-oxo-6-ethyl-6,7,8,9-tetrahydro-5H-benzocyclohepten-2-yloxy)acetic acid Step 1

2-Methoxy-3,4-dichloro-6-ethyl-6,7,8,9-tetrahydro-5H-benzocyclohepten-5-one

2-Methoxy-3,4-dichloro-6,7,8,9-tetrahydro-5H-benzocyclohepten-5-one as obtained in Example VI, Step 1, (12 g., 0.046 mole) is dissolved in t-butyl alcohol (250 ml.). A stream of nitrogen is lead through the flask and the mixture is heated to reflux. Then a solution of potassium t-butoxide (0.1 mole) dissolved in t-butyl alcohol (175 ml.) is added rapidly. The dark solution is refluxed for one hour, then cooled to 20° C. and ethyl bromide (10.9 g., 0.1 mole) is added. The mixture is refluxed for 10 minutes. Potassium bromide precipitates and the reaction mixture becomes lighter in color. The mixture is cooled, water (25 ml.) is added and the mixture is evaporated to dryness. The crude product is washed with water, collected and air dried to provide 2- methoxy-3,4-dichloro-6-ethyl-6,7,8,9-tetrahydro-5H-benzocyclohepten- 5-one.

Step 2

2-Hydroxy-3,4-dichloro-6-ethyl-6,7,8,9-tetrahydro-5H-benzocyclohepten-5-one

By the process of Example VI, Step 2, but substituting for the 2-methoxy-3,4-dichloro-6,7,8,9-tetrahydro-5H-benzocyclohepten-5-one used therein an equivalent amount of 2-methoxy-3,4-dichloro-6-ethyl-6,7,8,9-tetrahydro- 5H-benzocyclohepten-5-one and conducting the reaction as described in Example VI, Step 2, there is obtained 2-hydroxy- 3,4-dichloro-6-ethyl-6,7,8,9-tetrahydro-5H-benzocyclohepten- 5-one.

Step 3

(3,4-Dichloro-5-oxo-6-ethyl-6,7,8,9-tetrahydro-5H-benzocyclohepten- 2-yloxy)acetic acid By the process of Example VI, Step 3, but substituting for the 2-hydroxy-3,4-dichloro-6,7,8,9-tetrahydro-5H- benzocyclohepten-5-one used therein, an equivalent amount of 2-hydroxy-3,4-dichloro-6-ethyl-6,7,8,9-tetrahydro-5H- benzocyclohepten-5-one and conducting the reaction as described in Example VI, Step 3, there is obtained (3,4- dichloro-5-oxo-6-ethyl-6,7,8,9-tetrahydro-5-H-benzocyclohepten- 2-yloxy)acetic acid.

EXAMPLE VIII (3,4-Dichloro-5-oxo-6-cyclopentyl-6,7,8,9-tetrahydro-5H-benzocyclohepten-2-yloxy)acetic acid Step 1

Diethyl Cyclopentyl-3-(3,4-dichloro-5-methoxyphenyl)propylmalonate 2,3-Dichloro-5-(3-bromopropyl)anisole (20 g., 0.088 mole) as obtained in Example C, Step 3, and diethyl cyclopentylmalonate (24 g., 0.106 mole) in dry ethanol is added dropwise to a boiling solution of dry ethanol containing dissolved sodium (2.024 g., 0.088 g. atom). The mixture is refluxed until it is no longer basic. The alcohol then is removed by distillation, the precipitated sodium bromide is dissolved by the addition of water and the mixture is extracted with a suitable solvent such as ether or benzene. The extracts are combined and washed with water and dried over $Na_2SO_4$. Evaporation of the solvent provides diethyl cyclopentyl-3-(3,4-dichloro-5- methoxyphenyl)propylmalonate.

Step 2
2-Cyclopentyl-5-(3,4-dichloro-5-methoxyphenyl)-pentanoic acid

The product from Example VIII, Step 1 (29 g., 0.065 mole) is refluxed in an aqueous-methanolic solution of potassium hydroxide (5.6 g., 0.1 mole) for five hours. The methanol then is distilled and the residual potassium salt is dissolved in water. The solution is filtered and acidified. The organic portion that separates is extracted with a solvent such as ether, benzene or chloroform. The extracts are washed with water and dried over sodium sulfate. The solvent then is evaporated and the substituted malonic acid so obtained is heated to a point where carbon dioxide is evolved and kept at this temperature until evolution of carbon dioxide ceases to obtain 2-cyclopentyl- 5-(3,4-dichloro-5-methoxyphenyl)pentanoic acid.

Step 3
2-Methoxy-3,4-dichloro-6-cyclopentyl-6,7,8,9-tetrahydro-5H- benzocyclohepten-5-one By the process of Example VI, Step 1, but substituting for the 5-(3,4-dichloro-5-methoxyphenyl)valeric acid used therein an equivalent amount of 2-cyclopentyl-5-(3,4- dichloro-5-methoxyphenyl)pentanoic acid, there is obtained 2-methoxy-3,4-dichloro-6-cyclopentyl-6,7,8,9-tetrahydro-5H- benzocyclohepten-5-one.

Step 4
2-Hydroxy-3,4-dichloro-6-cyclopentyl-6,7,8,9-tetrahydro-5H- benzocyclohepten-5-one By the process of Example VI, Step 2, but substituting for the 2-methoxy-3,4-dichloro-6,7,8,9-tetrahydro-5H- benzocyclohepten-5-one used therein an equivalent amount of 2-methoxy-3,4dichloro-6-cyclopentyl-6,7,8,9-tetrahydro- 5H-benzocyclohepten-5-one there is obtained 2-hydroxy-3,4- dichloro-6-cyclopentyl-6,7,8,9-tetrahydro-5H-benzocyclohepten- 5-one.

Step 5
(3,4-Dichloro-5-oxo-6cyclopentyl-6,7,8,9-tetrahydro-5H- benzocyclohepten-2-yloxy)acetic acid By the process of Example VI, Step 3, but substituting for the 2-hydroxy-3,4-dichloro-6,7,8,9-tetrahydro-5H-benzocyclohepten-5-one used therein an equivalent amount of 2-hydroxy-3,4-dichloro- 6-cyclopentyl-6,7,8,9-tetrahydro- 5H-benzocyclohepten-5-one there is obtained (3,4-dichloro-5- oxo-6-cyclopentyl-6,7,8,9-tetrahydro-5H-benzocyclohepten-2-yloxy)acetic acid.

EXAMPLE IX (3,4-Dichloro-5-oxo-6-cyclopentyl-6-methyl-6,7,8,9-tetrahydro- 5H-benzocyclohepten-2-yloxy)acetic acid Step 1
2-Methoxy-3,4-dichloro-6-cyclopentyl-6-methyl-6,7,8,9-tetrahydro- 5H-benzocyclohepten-5-one By the process of Example VII, Step 1, but substituting for the 2-methoxy-3,4-dichloro-6,7,8,9-tetrahydro-5H- benzocyclohepten-5-one used therein an equivalent amount of 2-methoxy-3,4-dichloro-6-cyclopentyl-6,7,8,9-tetrahydro- 5H-benzocyclohepten-5-one, as obtained in Example VIII, Step 3, and for the ethyl bromide used therein, an equivalent quantity of methyl iodide, there is obtained 2-methoxy-3,4- dichloro-6-cyclopentyl-6-methyl-6,7,8,9-tetrahydro-5H-benzocyclohepten-5-one.

Step 2
2-Hydroxy-3,4-dichloro-6-cyclopentyl-6-methyl-6,7,8,9-tetrahydro- 5H-benzocyclohepten-5-one By the process of Example VI, Step 2, but substituting for the 2-methoxy-3,4-dichloro-6,7,8,9-tetrahydro-5H-benzocyclohepten- 5one used therein an equivalent amount of 2-methoxy-3,4-dichloro-6-cyclopentyl-6-methyl-6,7,8,9-tetrahydro- 5H-benzocyclohepten-5-one there is obtained 2-hydroxy- 3,4-dichloro-6-cyclopentyl-6-methyl-6,7,8,9-tetrahydro-5H-benzocyclohepten-5-one.

Step 3
(3,4-Dichloro-5-oxo-6-cyclopentyl-6-methyl-6,7,8,9-tetrahydro- 5H-benzocyclohepten-2-yloxy)acetic acid By the process of Example VI, Step 3, but substituting for the 2-hydroxy-3,4-dichloro-6,7,8,9-tetrahydro-5H-benzocyclohepten-5-one used therein an equivalent amount of 2-hydroxy-3,4-dichloro-6-cyclopentyl-6-methyl-6,7,8,9- tetrahydro-5H-benzocyclohepten-5-one there is obtained (3,4-dichloro-5-oxo-6-cyclopentyl-6methyl-6,7,8,9-tetrahydro- 5H-benzocyclohepten-2-yloxy) acetic acid.

EXAMPLE X 5-(3,4-Dichloro-5-oxo-6-cyclopentyl-6,7,8,9-tetrahydro-5H- benzocyclohepten-2-yloxymethyl)tetrazole)

Step 1
(3,4-Dichloro-5-oxo-6-cyclopentyl-6,7,8,9-tetrahydro-5H-benzocyclohepten- 2-yloxy)acetonitrile 2-Hydroxy-3,4-dichloro-6-cyclopentyl-6,7,8,9-tetrahydro- 5H-benzocyclohepten-5-one, as obtained in Example VIII, Step 4 (23.5 g., 0.075 mole), potassium carbonate (23 g.), and chloroacetonitrile (7.5 g., 0.1 mole) in DMF (100 ml.) is stirred at 55°–60°C. for two hours and then poured into water. The (3,4-dichloro-5-oxo-6-cyclopentyl-6,7,8,9-tetrahydro-5H-benzocyclohepten-2-yloxy) acetonitrile that separates is collected and air-dried.

Step 2
5-(3,4-Dichloro-5-oxo-6-cyclopentyl-6,7,8,9-tetrahydro-5H-benzocyclohepten-2-yloxymethyl)tetrazole To a solution of (3,4-dichloro-5-oxo-6-cyclopentyl-6,7,8,9-tetrahydro-5H-benzocyclohepten-2-yloxy)acetonitrile (5.7 g., 0.0165 mole) in DMF (25 ml.) is added sodium azide (1.26 g., 0.0194 mole) and ammonium chloride (1.05 g., 0.0194 mole). The mixture is heated at 85°–90° C. for one hour, cooled and poured into ice water. The mixture is acidified with 6 N HCl. The gummy solid that forms is triturated with butyl chloride and then crystallized from butyl chloride-methanol to obtain 5-(3,4-dichloro-5-oxo-6-cyclopentyl-6,7,8,9-tetrahydro-5H-benzocyclohepten-2-yloxymethyl)tetrazole.

EXAMPLE XI

1-Oxo-2-cyclopentyl-(2,7,8-trimethyl-1,2,3,4-tetrahydro-6-naphthyloxy)acetic acid Step 1
2-Cyclopentyl-2,7,8-trimethyl-6-methoxy-1-tetralone 2-Cyclopentyl-6-methoxy-7,8-dimethyl-1-tetralone (Example V, Step 4) (12.5 g., 0.046 mole) is dissolved in t-butyl alcohol (250 ml.) under a stream of nitrogen. The mixture is heated to reflux and then a solution of potassium t-butoxide (7.5 g., 0.067 mole) dissolved in t-butyl alcohol (175 ml.) is added. The dark solution is refluxed for 1 hour, cooled to 20° C. and methyl iodide (14.2 g., 0.1 mole) is added. The mixture is refluxed for 10 minutes. Potassium iodide precipitates and the color of the mixture becomes lighter. The mixture is cooled, water (25 ml.) is added and the mixture is evaporated to dryness. The crude product is collected, washed with water and air dried to obtain 2-cyclopentyl-2,7,8-trimethyl-6-methoxy-1-tetralone.

Step 2

2-Cyclopentyl-2,7,8-trimethyl-6-hydroxy-1-tetralone

By the procedure of Example II, Step 4, but substituting for the 6-methoxy-7,8-dichloro-1-tetralone there used, an equivalent amount of 2,7,8-trimethyl-2-cyclopentyl-6-methoxy-1-tetralone, 2-cyclopentyl-2,7,8-trimethyl-6-hydroxy-1-tetralone is obtained.

Step 3

(1-Oxo-2-cyclopentyl-2,7,8-trimethyl-1,2,3,4-tetrahydro-6-naphthyloxy)acetic acid By the process of Example II, Step 5, but substituting for the 6-hydroxy-7,8-dichloro-1-tetralone there used an equivalent amount of 2-cyclopentyl-2,7,8-trimethyl-6-hydroxy-1-tetralone, (1-oxo-2-cyclopentyl-2,7,8,-trimethyl-1,2,3,4-tetrahydro-6-naphthyloxy)acetic acid is obtained.

EXAMPLE XII

N,N-Diethyl-(1-oxo-2-cyclopentyl-7,8-dichloro-1,2,3,4-tetrahydro-6-naphthyloxy)acetamide The product of Example I, Step 5 (4.0 g., 0.02 mole) is added to thionyl chloride (11 g.) and the mixture is refluxed until HCl and $SO_2$ are no longer evolved (about 1 hour). The excess thionyl chloride is evaporated. The residue is dissolved in benzene and a solution of diethylamine (3.6 g., 0.05 mole) in benzene is added. The mixture is kept for 1 hour and then evaporated to dryness. The residue is washed with water, 10% sodium bicarbonate and with water and airdried to obtain N,N-diethyl-(1-oxo-2-cyclopentyl-7,8-dichloro-1,2,3,4-tetrahydro-6-naphthyloxy)acetamide.

In an analogous manner, other N,N-dialkyl-acetamide derivatives of the compounds of this example, as well as the other compounds of Formula I where Z is carboxyl, are prepared by employing the appropriate diloweralkylamine such as dimethylamine, methylethylamine and the like.

EXAMPLE XIII (3,4-Dichloro-5-oxo-6-cyclopentyl-6-methyl-6,7,8,9-tetrahydro-5H-benzocyclohepten-2-yloxy)acetamide (3,4-Dichloro-5-oxo-6-cyclopentyl-6-methyl-6,7,8,9-tetrahydro-5H-benzocyclohepten-2-yloxy)acetic acid from Example IX, Step 3 (7.7 g., 0.02 mole) is added to thionyl chloride (2.2 g.) and the mixture is refluxed until HCl and $SO_2$ are no longer involved. The excess $SOCl_2$ then is evaporated. The residue is dissolved in benzene and a gentle stream of ammonia is lead into the solution until no more ammonia is absorbed. The mixture then is evaporated to dryness. The residue is washed next with water, 10% sodium bicarbonate and with water and air dried to obtain (3,4-dichloro-5-oxo-6-cyclopentyl-6-methyl-6,7,8,9-tetrahydro-5H-benzocyclohepten-2-yloxy)acetamide.

In an analogous manner, the acetamides of the other compounds of Formula I are prepared.

The novel compounds of this invention are diuretic and saluretic agents which can be administered in a wide variety of therapeutic dosages in conventional vehicles as, for example, by oral administration in the form of a tablet or by parenteral routes such as by intravenous injection or rectally employing suppositories. Also, the daily dosage of the products may be varied over a wide range, 5 to 500 mg. It can be administered, for example, in the form of tablets containing 5, 10, 25, 50, 100, 150, 250 and 500 milligrams of the active ingredient for the symptomatic adjustment of the dosage to the patient to be treated.

A suitable unit dosage form of the products of this invention can be administered by mixing 50 milligrams of a 1-oxo-(7,8disubstituted-1,2,3,4-tetrahydro-6-naphthyloxy) and (3,4-disubstituted-5-oxo-6,7,8,9-tetrahydro-5H-benzocyclohepten-2-yloxy)acetic acid or a suitable acid salt, ester or amide derivative thereof, with 149 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capsules may be employed. Compressed tablets, pills, or other desired unit dosages can be prepared to incorporate the compounds of this invention by conventional methods and, if desired, can be made up as elixirs, as injectable solutions or suppositories by methods well known to pharmacists.

It is also within the scope of this invention to combine two or more of the compounds of this invention in a unit dosage form or to combine one or more of the compounds of this invention with other known diuretics and saluretics or with other desired therapeutic and/or nutrative agents in dosage unit form.

The following example is included to illustrate the preparation of a representative dosage form.

| Dry-Filled Capsules Containing 50 Mg. of Active Ingredient Per Capsule | |
|---|---|
| | Mg. per Capsule |
| (1-Oxo-2-cyclopentyl-7,8-dichloro-1,2,3,4-tetrahydro-6-naphthyloxy)-acetic acid | 50 |
| Lactose | 149 |
| Magnesium Stearate | 1 |
| | 200 |

The (1-oxo-2-cyclopentyl-7,8-dichloro-1,2,3,4-tetrahydro-6-naphthyloxy)acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

What is claimed is:

1. A compound of the formula:

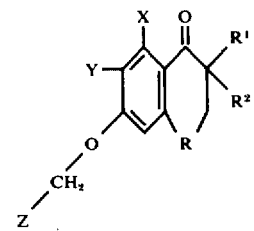

wherein R is methylene; $R^1$ is cyclopentyl; $R^2$ is $C_1$ to $C_4$ alkyl or hydrogen; X and Y are independently halogen or methyl; and Z is carboxy or a carboxylate salt of physiologically acceptable non-toxic cations.

* * * * *